United States Patent
Itoh et al.

(10) Patent No.: US 9,663,490 B2
(45) Date of Patent: May 30, 2017

(54) PROCESS FOR MAKING REVERSE TRANSCRIPTASE INHIBITORS

(71) Applicant: Merck Sharp & Dohme Corp., Rahway, NJ (US)

(72) Inventors: Tetsuji Itoh, Somerset, NJ (US); Ingyu Jeon, Somerset, NJ (US); Ian Mangion, Cranford, NJ (US); Gang Qian, South Brunswick, NJ (US); Benjamin D. Sherry, New York, NY (US); Donald R. Gauthier, Westfield, NJ (US); Yang Cao, Scotch Plains, NJ (US)

(73) Assignee: Merck Sharp & Dohme Corp., Rahway, NJ (US)

( * ) Notice: Subject to any disclaimer, the term of this patent is extended or adjusted under 35 U.S.C. 154(b) by 0 days.

(21) Appl. No.: 14/649,837

(22) PCT Filed: Dec. 4, 2013

(86) PCT No.: PCT/US2013/072964
§ 371 (c)(1),
(2) Date: Jun. 4, 2015

(87) PCT Pub. No.: WO2014/089140
PCT Pub. Date: Jun. 12, 2014

(65) Prior Publication Data
US 2015/0329521 A1    Nov. 19, 2015

Related U.S. Application Data

(60) Provisional application No. 61/733,504, filed on Dec. 5, 2012.

(51) Int. Cl.
*C07D 401/06*    (2006.01)

(52) U.S. Cl.
CPC .................. *C07D 401/06* (2013.01)

(58) Field of Classification Search
None
See application file for complete search history.

(56) References Cited

U.S. PATENT DOCUMENTS

| 2010/0034813 A1* | 2/2010 | Xia | C07D 249/08 424/133.1 |
| 2010/0256181 A1* | 10/2010 | Tucker | C07D 471/04 514/303 |
| 2011/0245296 A1* | 10/2011 | Burch | A61K 31/4439 514/340 |

FOREIGN PATENT DOCUMENTS

EP    1238975    9/2002

OTHER PUBLICATIONS

Cowden, et al., "A New Synthesis of 1,2,4-Triazolin-5ones: Application to the Convergent Synthesis of an NK1 Antagonist", Tetrahedron letters, 2000, pp. 8661-8664, vol. 41, No. 44.
Eugene, F., et al, "N-Ethyldiisopropylamine and Sulfur Dioxide Solutions. 2. Reactions with Conjugate Acceptors", J. Org. Chem., 1994, pp. 2599-2603, vol. 59.

* cited by examiner

*Primary Examiner* — Timothy R Rozof
(74) *Attorney, Agent, or Firm* — Carol S. Quagliato; Catherine D. Fitch

(57) ABSTRACT

The present invention is directed to a novel process for synthesizing 3-(substituted phenoxy)-1-[(5-oxo-4,5-dihydro-1H-1,2,4-triazol-3-yl)methyl])-pyridin-2(1H)-one derivatives. The compounds synthesized by the processes of the invention are HIV reverse transcriptase inhibitors useful for inhibiting reverse transcriptase, HIV replication and the treatment of human immunodeficiency virus infection in humans.

25 Claims, No Drawings

PROCESS FOR MAKING REVERSE TRANSCRIPTASE INHIBITORS

RELATED APPLICATIONS

This application is a 35 U.S.C. §371 filing from International Application No. PCT/US2013/072964, filed Dec. 4, 2013, which claims the benefit of U.S. Provisional Application No. 61/733,504, filed Dec. 5, 2012. Each of the aforementioned applications is herein incorporated by reference in its entirety.

BACKGROUND OF THE INVENTION

The retrovirus designated human immunodeficiency virus (HIV), particularly the strains known as HIV type-1 (HIV-1) and type-2 (HIV-2), have been etiologically linked to the immunosuppressive disease known as acquired immunodeficiency syndrome (AIDS). HIV seropositive individuals are initially asymptomatic but typically develop AIDS related complex (ARC) followed by AIDS. Affected individuals exhibit severe immunosuppression which makes them highly susceptible to debilitating and ultimately fatal opportunistic infections. Replication of HIV by a host cell requires integration of the viral genome into the host cell's DNA. Since HIV is a retrovirus, the HIV replication cycle requires transcription of the viral RNA genome into DNA via an enzyme known as reverse transcriptase (RT).

Reverse transcriptase has three known enzymatic functions: The enzyme acts as an RNA-dependent DNA polymerase, as a ribonuclease, and as a DNA-dependent DNA polymerase. In its role as an RNA-dependent DNA polymerase, RT transcribes a single-stranded DNA copy of the viral RNA. As a ribonuclease, RT destroys the original viral RNA and frees the DNA just produced from the original RNA. And as a DNA-dependent DNA polymerase, RT makes a second, complementary DNA strand using the first DNA strand as a template. The two strands form double-stranded DNA, which is integrated into the host cell's genome by the integrase enzyme.

It is known that compounds that inhibit enzymatic functions of HIV RT will inhibit HIV replication in infected cells. These compounds are useful in the prophylaxis or treatment of HIV infection in humans. Among the compounds approved for use in treating HIV infection and AIDS are the RT inhibitors 3'-azido-3'-deoxythymidine (AZT), 2',3'-dideoxyinosine (ddI), 2',3'-dideoxycytidine (ddC), d4T, 3TC, nevirapine, delavirdine, efavirenz, abacavir, emtricitabine, and tenofovir.

The RT inhibitor 3-chloro-5-({1-[(4-methyl-5-oxo-4,5-dihydro-1H-1,2,4-triazol-3-yl)methyl]-2-oxo-4-(trifluoromethyl)-1,2-dihydropyridin-3-yl}oxy)benzonitrile, related compounds and methods for making the same are illustrated in WO 2011/120133 A1, published on Oct. 6, 2011, and US 2011/0245296 A1, published on Oct. 6, 2011, both of which are hereby incorporated by reference in their entirety. The present invention is directed to a novel process for synthesizing 3-(substituted phenoxy)-1-[(5-oxo-4,5-dihydro-1H-1,2,4-triazol-3-yl)methyl])pyridin-2(1H)-one derivatives and intermediates useful in the synthesis thereof. The compounds synthesized by the processes of the invention are HIV reverse transcriptase inhibitors useful for inhibiting reverse transcriptase, HIV replication and the treatment of human immunodeficiency virus infection in humans.

SUMMARY OF THE INVENTION

The present invention is directed to a novel process for synthesizing 3-(substituted phenoxy)-1-[(5-oxo-4,5-dihydro-1H-1,2,4-triazol-3-yl)methyl])-pyridin-2(1H)-one derivatives. The compounds synthesized by the processes of the invention are HIV reverse transcriptase inhibitors useful for inhibiting reverse transcriptase, HIV replication and the treatment of human immunodeficiency virus infection in humans.

DETAILED DESCRIPTION OF THE INVENTION

The invention is directed to a method for synthesizing compounds of Formula I

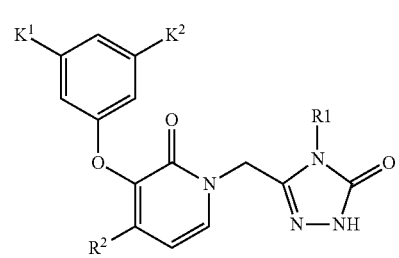

I wherein $R^1$ is $C_{1-6}$alkyl, $K^1$ and $K^2$ are independently $CH_3$, $CF_3$, $CHF_2$, $CH_2CF_3$, $OCH_3$, Cl, Br, F, CN or $SCH_3$, and $R^2$ is $CF_3$, Cl or Br, comprising introducing a nitrogen protecting group PG into a compound of Formula A

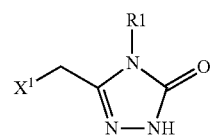

A wherein $X^1$ is a leaving group, to make a compound of Formula B

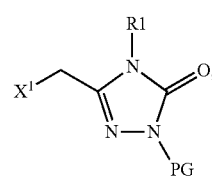

B reacting a compound of Formula B with a compound of Formula C

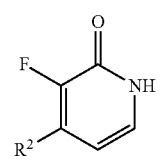

C in the presence of a first base selected from an inorganic base or a tertiary amine base in a first polar aprotic solvent to make a compound of Formula D

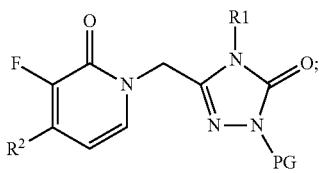

coupling the compound of Formula D with a compound of Formula E

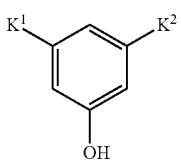

to make a compound of Formula F

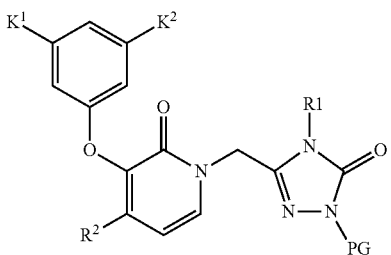

by way of step (1) or step (2) wherein:
step (1) comprise adding the compound of Formula E to the reaction mixture comprising the compound of Formula D from the previous step without further isolation to make a compound of Formula F, and
step (2) comprises isolating the compound of Formula D from the previous step and reacting the compound of Formula D with the compound of Formula E in the presence of a second base selected from an inorganic base or a tertiary amine base in a second polar aprotic solvent to yield the compound of Formula F,
and deprotecting the nitrogen protecting group PG in the compound of Formula F to yield a compound of Formula I.

The term "nitrogen protecting group" means a substituent that protects a nitrogen atom in a reaction from a reagent or chemical environment. Nitrogen protecting groups are well known in the art and include for example, t-butyl, vinyl, phenyl, benzyl, p-methoxybenzyl, 3,4-dimethoxybenzyl, p-nitrobenzyl, benzhydryl, trityl, trialkylsilyl, methoxymethyl ether, (2,2,2-trichloroethoxy)methyl and 2-(trimethylsilyl)ethoxy)methyl. Methods for deprotecting a nitrogen are also well within the skill of one having ordinary skill in the art. In an embodiment, the invention encompasses the process described herein wherein PG is selected from the group consisting of: $C_{1-6}$ alkyl, vinyl, C(O)—O-L, C(O)-L, aryl, hetroaryl, benzyl, benzhydryl, trityl, anthranyl and $C_{1-6}$alkoxymethyl, wherein aryl, heteroaryl, benzyl, benzyhydryl and trityl optionally are substituted with 1 to 3 substituents independently selected from methoxy and nitro, $C_{1-6}$alkoxymethyl is optionally substituted with trimethylsilyl and L is $C_{1-6}$alkyl, aryl or benzyl. In another embodiment, the invention encompasses the process described herein wherein PG is 2-methoxypropan-2-yl.

The term "leaving group" means an atom or atom group that leaves from a substrate in a substitution or elimination reaction and includes for example halogen and sulfonate. In an embodiment, the invention encompasses the process described herein wherein $X^1$ is selected from the group consisting of: halogen, OMs (mesylate), OTs (tosylate), OBs (besylate), $OP(O)(OR^i)_4$, $OC(O)R^i$, $OC(O)OR^i$ and $OC(O)NR^iR^{ii}$, wherein $R^i$ and $R^{ii}$ are independently selected from H and $C_{1-6}$alkyl. In another embodiment, the invention encompasses the process described herein wherein $X^1$ is chloro.

The first base is selected from an inorganic base or a tertiary amine base. Inorganic bases include, for example, sodium hydroxide, lithium hydroxide, potassium hydroxide, sodium carbonate, lithium carbonate, potassium carbonate, cesium hydroxide, cesium carbonate, sodium hydrogen carbonate, potassium hydrogen carbonate, lithium hydrogen carbonate, lithium fluoride, sodium fluoride, potassium fluoride, cesium fluoride, lithium tert-butoxide, sodium tert-butoxide, potassium tert-butoxide, sodium phosphate and potassium phosphate. Tertiary amine bases include for example trimethylamine, dimethylethylamine, triethylamine, 1,4-diazobicyclo-[2,2,2]-octane, diisopropylethylamine, dicyclohexylethylamine. Suitable polar aprotic solvents include for example tetrahydrofuran, ethyl acetate, acetone, dimethylformamide, acetonitrile, dimethyl sulfoxide, dimethylacetomide, N-methylpyrrolidinone. The first base and second base are selected independently from each other. Likewise, the first polar aprotic solvent and second polar aprotic solvent are also selected independently from each other.

In an embodiment, the invention encompasses the process described herein wherein the first base is potassium carbonate and the first polar aprotic solvent is dimethylformamide.

In an embodiment, the invention encompasses the process described herein wherein the compound of Formula F is made by step (1). In a further embodiment, the reaction of step (1) is heated to an elevated temperature. The term elevated temperature means above room temperature. In a further embodiment, the elevated temperature is about 95° C. to about 100° C.

In an embodiment, the invention encompasses the process described herein wherein the nitrogen protecting group PG in the compound of Formula F is deprotected by reacting the compound of Formula F with an acid.

Another embodiment of the invention encompasses the method for synthesizing a compound of Formula I as described herein further comprising synthesizing the compound of Formula A by condensing glycolic acid with a compound of Formula G

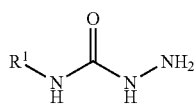

to yield a compound of Formula H

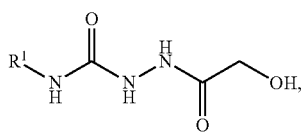

cyclizising the compound of Formula H under first basic conditions to make a compound of Formula J

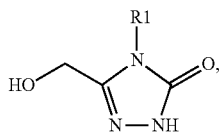

and replacing the alcohol with the leaving group $X^1$ by reacting the compound of Formula J with an activating agent to yield a compound of Formula A.

"Basic conditions" can be achieved by use of an appropriate base such as sodium hydroxide, potassium hydroxide, lithium hydroxide, cesium hydroxide, potassium carbonate, sodium carbonate, and lithium carbonate.

The replacement of the alcohol with the appropriate leaving group $X^1$ can be accomplished by techniques well known to those skilled in the art. For example, the alcohol can be replaced with chloride by reaction with thionyl chloride. The term "activating agent" means an agent capable of replacing the alcohol with a desired leaving group $X^1$ for example mesyl chloride, tosyl chloride, $(PhO)_2POCl$, oxalyl chloride, $SOCl_2$ and phosgene.

In an embodiment, the invention encompasses the process described herein wherein $X^1$ is chloro and the activating agent is $SOCl_2$.

In an embodiment, the invention encompasses the process described herein wherein first basic conditions means in the presence of sodium hydroxide.

Another embodiment encompasses the method for synthesizing a compound of Formula I as described herein further comprising synthesizing the compound of Formula G by reacting a compound of Formula K

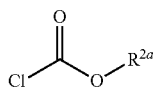

wherein $R^{2a}$ is selected from aryl or heteroaryl, wherein said aryl or heteroaryl are optionally substituted with one or more substituents up to the maximum number allowed by valence selected from the group consisting of: halogen, $C_{1-6}$ alkyl, $C_{1-6}$ haloalkyl, OH, O—$C_{1-6}$ alkyl, O—$C_{1-6}$ haloalkyl, $N(R^A)R^B$, $C(O)N(R^A)R^B$, $C(O)R^A$, $CO_2R^A$, $SO_2R^A$, $N(R^A)C(O)N(R^A)R^B$, or $N(R^A)CO_2R^B$;
$R^A$ and $R^B$ are independently selected from H, $C_{1-6}$ alkyl and $C_{3-6}$ cycloalkyl, wherein said $C_{1-6}$ alkyl and $C_{3-6}$ cycloalkyl are optionally substituted with one or more substituents up to the maximum number allowed by valence selected from the group consisting of: halogen, OH, CN, $C_{1-4}$ alkoxy, $C_{3-6}$ cycloalkyl and phenyl;
with a compound of Formula L

under second basic conditions to yield a compound of Formula M

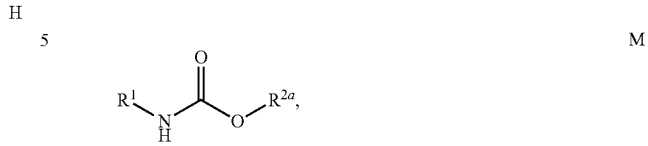

reacting the compound of Formula M with hydrazine to yield a compound of Formula G.

Second basic condition means "basic conditions" as described above, but is independent of first basic conditions.

The term "aryl" refers to phenyl, naphthyl, and anthranyl.

The term heteroaryl is independently (i) a 5- or 6-membered heteroaromatic ring containing from 1 to 4 heteroatoms independently selected from N, O and S, wherein each N is optionally in the form of an oxide, or (ii) a 9- or 10-membered heterobicyclic, fused ring system containing from 1 to 4 heteroatoms independently selected from N, O and S, wherein either one or both of the rings contain one or more of the heteroatoms, at least one ring is aromatic, each N is optionally in the form of an oxide, and each S in a ring which is not aromatic is optionally S(O) or $S(O)_2$. Examples of heteroaryl include, for example, pyridyl (also referred to as pyridinyl), pyrrolyl, pyrazinyl, pyrimidinyl, pyridazinyl, triazinyl, thienyl, furanyl, imidazolyl, pyrazolyl, triazolyl, oxazolyl, isooxazolyl, oxadiazolyl, oxatriazolyl, thiazolyl, isothiazolyl, thiadiazolyl, indolyl, quinolinyl, isoquinolinyl, and quinoxalinyl In an embodiment, the invention encompasses the process described herein wherein second basic conditions means in the presence of sodium hydroxide.

The invention also encompasses any of the embodiments described above wherein in the compound of Formula I $K^1$ is Cl, $K^2$ is CN, $R^1$ is $CH_3$ and $R^2$ is $CF_3$.

Another embodiment of the invention encompasses a method for synthesizing a compound of Formula D

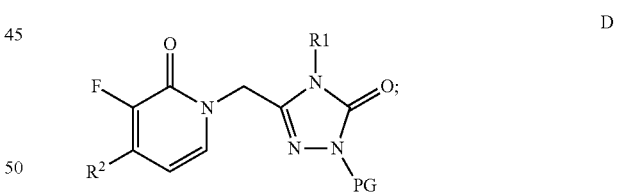

wherein $R^1$ is $C_{1-6}$alkyl and $R^2$ is $CF_3$, Cl or Br, comprising reacting a compound of Formula B

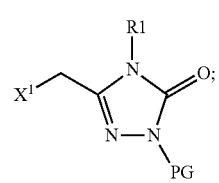

wherein PG is a nitrogen protecting group with a compound of Formula C

in the presence of a first base selected from an inorganic base or a tertiary amine base in a first polar aprotic solvent to make the compound of Formula D.

Another embodiment of the invention encompasses a method for synthesizing a compound of Formula A

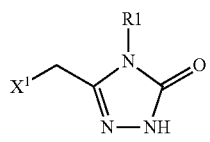

wherein R¹ is $C_{1-6}$ alkyl and X¹ is a leaving group, comprising condensing glycolic acid with a compound of Formula G

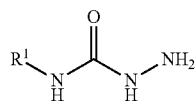

to yield a compound of Formula H

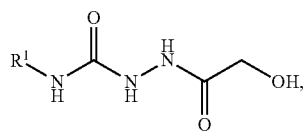

cyclizising the compound of Formula H under first basic conditions to make a compound of Formula J

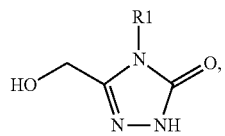

and replacing the alcohol with the leaving group X¹ by reacting the compound of Formula J with an activating agent to yield a compound of Formula A.

Another embodiment of the invention encompasses method for synthesizing a compound of Formula I

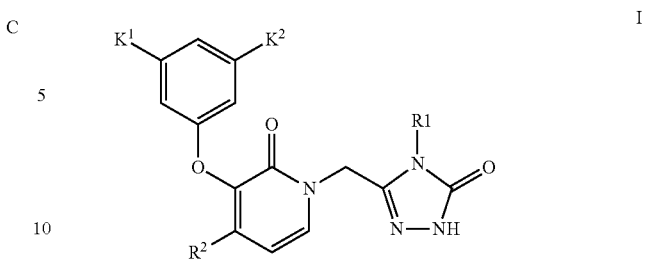

wherein R¹ is $C_{1-6}$ alkyl, K¹ and K² are independently $CH_3$, $CF_3$, $CHF_2$, $CH_2CF_3$, $OCH_3$, Cl, Br, F, CN or $SCH_3$, and R² is $CF_3$, Cl or Br, comprising reacting a compound of Formula A

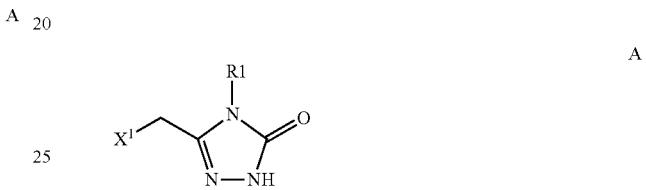

wherein X¹ is a leaving group, with a compound of Formula C

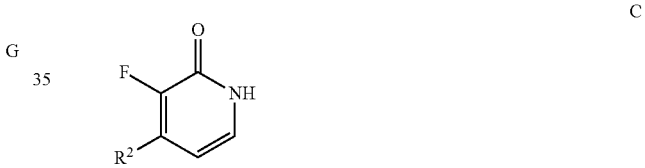

in the presence of a first base selected from an inorganic base or a tertiary amine base in a first polar aprotic solvent to make a compound of Formula D1

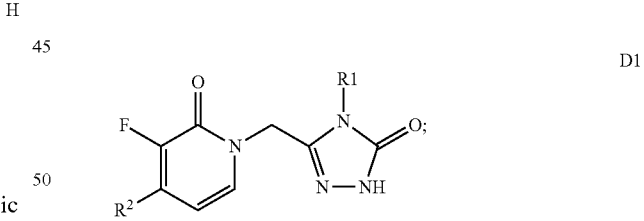

coupling the compound of Formula D1 with a compound of Formula E

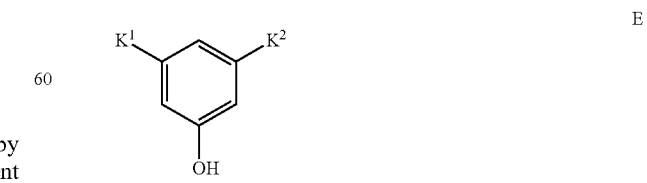

to make a compound of Formula I by way of step (1) or step (2) wherein:

step (1) comprise adding the compound of Formula E to the reaction mixture comprising the compound of Formula D1 from the previous step without further isolation to make a compound of Formula I, and step (2) comprises isolating the compound of Formula D1 from the previous step and reacting the compound of Formula D1 with the compound of Formula E in the presence of a second base selected from an inorganic base or a tertiary amine base in a second polar aprotic solvent to yield the compound of Formula I.

Another embodiment of the invention encompasses a method for synthesizing a compound of Formula I

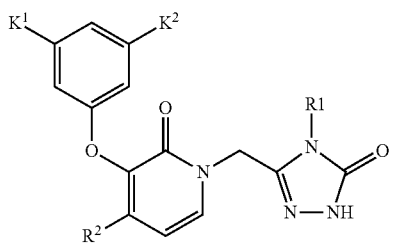

wherein $R^1$ is $C_{1-6}$ alkyl, $K^1$ and $K^2$ are independently $CH_3$, $CF_3$, $CHF_2$, $CH_2CF_3$, $OCH_3$, Cl, Br, F, CN or $SCH_3$, and $R^2$ is $CF_3$, Cl or Br, comprising
coupling a compound of Formula A

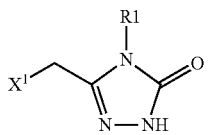

wherein $X^1$ is a leaving group, with a compound of Formula N

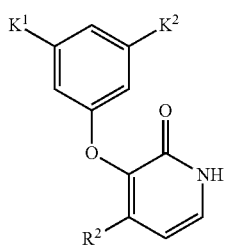

in the presence of a first base selected from an inorganic base or a tertiary amine base in a first polar aprotic solvent to yield a compound of Formula I. Within this embodiment the invention encompasses the foregoing process wherein the compound of Formula A is not isolated after its synthesis and in situ reacted directly with the compound of Formula N. Also within this embodiment the invention encompasses the foregoing process wherein $X^1$ is selected from the group consisting of: halogen, OMs, OTs, OBs, $OP(O)(OR^i)_4$, $OC(O)R^i$, $OC(O)OR^i$ and $OC(O)NR^iR^{ii}$, wherein $R^i$ and $R^{ii}$ are independently selected from H and $C_{1-6}$alkyl. In a further embodiment the invention encompasses the foregoing process for synthesizing the compound of Formula I wherein $X^1$ is chloro. In a further embodiment, the invention encompasses the foregoing process for synthesizing the compound of Formula I wherein the first base is N,N-Diisopropylethylamine and the first polar aprotic solvent is N-methylpyrrolidinone.

Another embodiment of the invention encompasses the foregoing method for synthesizing a compound of Formula I further comprising synthesizing the compound of Formula A by condensing glycolic acid with a compound of Formula G

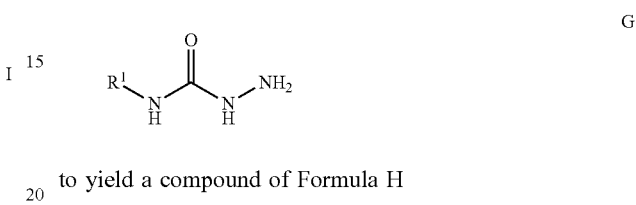

to yield a compound of Formula H

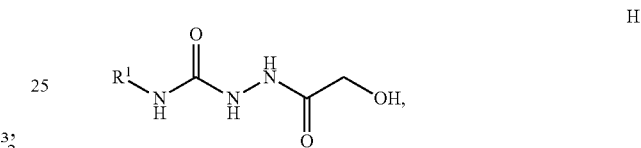

cyclizing the compound of Formula H under first basic conditions to make a compound of Formula J

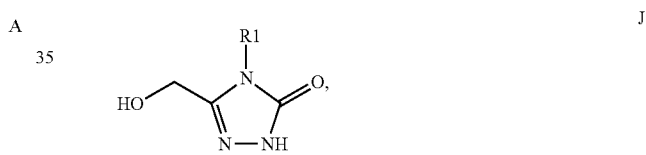

and replacing the alcohol with the leaving group $X^1$ by reacting the compound of Formula J with an activating agent to yield a compound of Formula A. Within this embodiment, the invention encompasses the foregoing method for synthesizing a compound of Formula I wherein $X^1$ is chloro and the activating agent is $SOCl_2$. Also within this embodiment, the invention encompasses the foregoing method for synthesizing a compound of Formula I wherein basic conditions means in the presence of sodium hydroxide.

Another embodiment of the invention encompasses the foregoing method for synthesizing a compound of Formula I further comprising synthesizing the compound of Formula G by reacting a compound of Formula K

wherein $R^{2a}$ is selected from aryl or heteroaryl, wherein said aryl or heteroaryl are optionally substituted with one or more substituents up to the maximum number allowed by valence selected from the group consisting of: halogen, $C_{1-6}$ alkyl, $C_{1-6}$ haloalkyl, OH, O—$C_{1-6}$ alkyl, O—$C_{1-6}$ haloalkyl, $N(R^A)R^B$, $C(O)N(R^A)R^B$, $C(O)R^A$, $CO_2R^A$, $SO_2R^A$, $N(R^A)C(O)N(R^A)R^B$, or $N(R^A)CO_2R^B$;

$R^A$ and $R^B$ are independently selected from H, $C_{1-6}$ alkyl and $C_{3-6}$ cycloalkyl, wherein said $C_{1-6}$ alkyl and $C_{3-6}$ cycloalkyl are optionally substituted with one or more substituents up to the maximum number allowed by valence selected from the group consisting of: halogen, OH, CN, $C_{1-4}$ alkoxy, $C_{3-6}$ cycloalkyl and phenyl;

with a compound of Formula L

under second basic conditions to yield a compound of Formula M

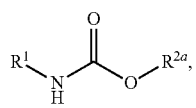

reacting the compound of Formula M with hydrazine to yield a compound of Formula G. Within this embodiment, the invention encompasses the foregoing method for synthesizing a compound of Formula I wherein second basic conditions means in the presence of sodium hydroxide.

The invention also encompasses any of the aforementioned methods for synthesizing the compound of Formula I wherein $K^1$ is Cl, $K^2$ is CN, $R^1$ is $CH_3$ and $R^2$ is $CF_3$.

The compound 3-chloro-5-({1-[(4-methyl-5-oxo-4,5-dihydro-1H-1,2,4-triazol-3-yl)methyl]-2-oxo-4-(trifluoromethyl)-1,2-dihydropyridin-3-yl}oxy)benzonitrile has the following chemical structure.

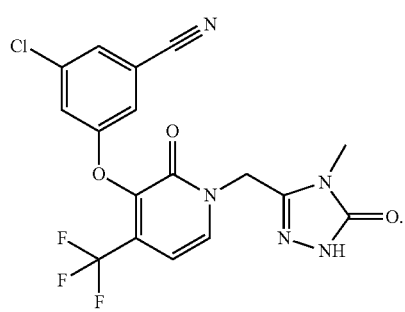 [SMILES: Cn1c(Cn2ccc(C(F)(F)F)c(Oc3cc(Cl)cc(C#N)c3)c2=O)n[nH]c1=O]

Anhydrous 3-chloro-5-({1-[(4-methyl-5-oxo-4,5-dihydro-1H-1,2,4-triazol-3-yl)methyl]-2-oxo-4-(trifluoromethyl)-1,2-dihydropyridin-3-yl}oxy)benzonitrile is known to exist in three crystalline forms—Form I, Form II and Form III. The differential scanning calorimetry (DSC) curve for crystalline anhydrous Form II shows an endotherm with an onset at 230.8° C., a peak maximum at 245.2° C., and an enthalpy change of 3.7 J/g, which is due to polymorphic conversion of anhydrous Form II to anhydrous Form I, and a second melting endotherm with an onset at 283.1° C., a peak maximum at 284.8° C., and an enthalpy change of 135.9 J/g, due to melting of Anhydrous Form I. Alternative production and the ability of this compound to inhibit HIV reverse transcriptase is illustrated in WO 2011/120133 A1, published on Oct. 6, 2011, and US 2011/0245296 A1, published on Oct. 6, 2011, both of which are hereby incorporated by reference in their entirety.

The process of the present invention offers greater efficiency, reduced waste, and lower cost of goods relative to the methods for making the subject compounds existing at the time of the invention. Particularly, the late stage cyanation and methylation steps are not required.

The following examples illustrate the invention. Unless specifically indicated otherwise, all reactants were either commercially available or can be made following procedures known in the art. The following abbreviations are used:

ABBREVIATIONS

DMF=dimethylformamide
NMP=N-methylpyrrolidinone
IPA=isopropyl alcohol
NPA=n-propyl alcohol
LC=liquid chromatography
LCAP=Liquid chromatography area percent
Me=methyl Example 1

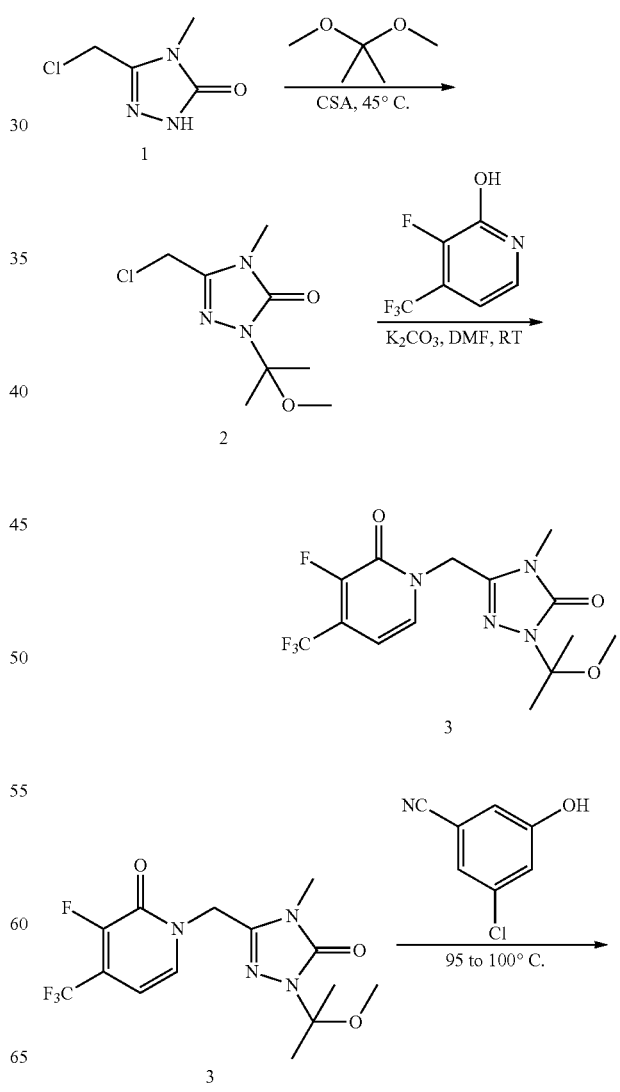

-continued

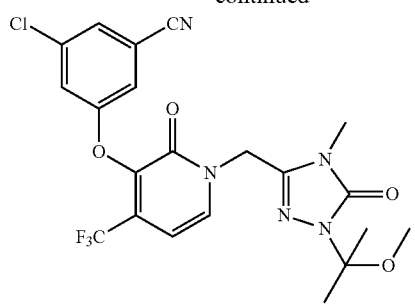

4

Step 2

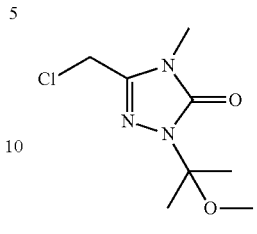

HCl
RT
→

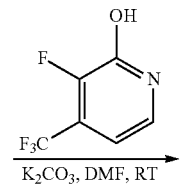

K₂CO₃, DMF, RT
→

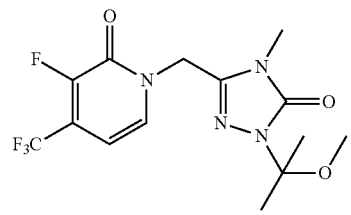

3

3-Fluoro-1-((1-(2-methoxypropan-2-yl)-4-methyl-5-oxo-4,5-dihydro-1H-1,2,4-triazol-3-yl)methyl)-4-(trifluoromethy)pyridin-2(1H)-one (3)

A mixture of 2 (100 mg, 93.1% purity, 0.49 mmol), pyridone (117 mg, 97.6% purity, 0.49 mmol) and K₂CO₃ (82 mg, 0.59 mmol) in DMF (0.5 ml) was aged with stirring at ambient temperature for 3 h. After the reaction was completed, the batch was taken on to the next step without further work up or isolation.

Step 3

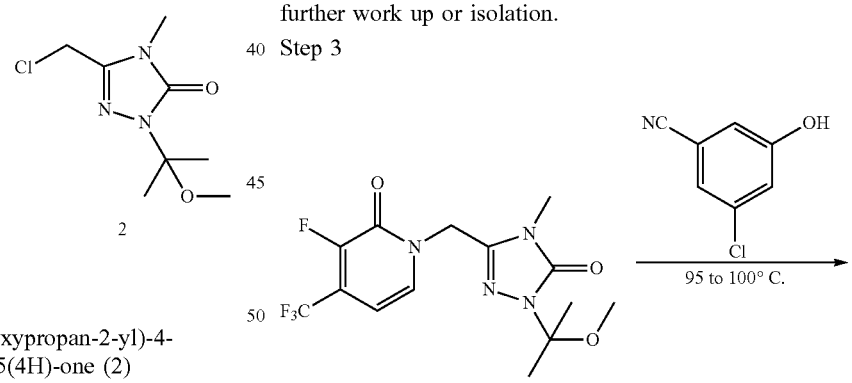

95 to 100° C.
→

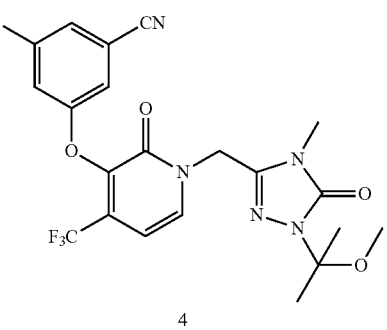

4

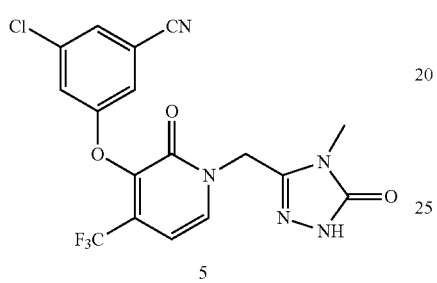

5

Step 1

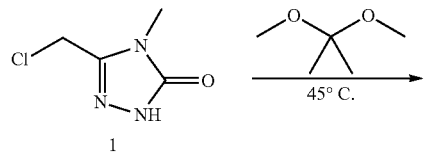

45° C.
→

3-(Chloromethyl)-1-(2-methoxypropan-2-yl)-4-methyl-1H-1,2,4-triazol-5(4H)-one (2)

A 100 ml round bottom flask equipped with stir bar and a nitrogen inlet was charged with 1 (5 g, 33.9 mmol) and (1S)-(+)-10-camphorsulfonic acid (0.39 g, 1.694 mmol) at ambient temperature. After 2,2-dimethoxy propane (36.0 g, 339 mmol) was charged at ambient temperature, the resulting mixture was heated to 45° C. The resulting mixture was stirred under nitrogen at 45° C. for 18 hours and monitored by HPLC for conversion of the starting material (<5% by HPLC). After the reaction was completed, the batch was taken on to the next step without further work-up or isolation. ¹H NMR (CDCl₃, 500 MHz): 4.45 (s, 2H), 3.35 (s, 3H), 3.21 (s, 3H), 1.83 (s, 6H).

3-Chloro-5-((1-((1-(2-methoxypropan-2-yl)-4-methyl-5-oxo-4,5-dihydro-1H-1,2,4-triazol-3-yl)methyl)-2-oxo-4-(trifluoromethyl)-1,2-dihydropyridin-3-yl)oxy)benzonitrile (4)

To a mixture of compound 3 in DMF (reaction mixture from the previous step) was added 3-chloro-5-hydroxybenzonitrile (1.77 g, 11.5 mmol) at ambient temperature. The resulting mixture was then heated to 95-100° C. and held for 20 hours.

Upon completion (typically 18-20 hours), the reaction was cooled to room temperature, diluted with ethyl acetate and washed with water. The aqueous cut was back extracted with ethyl acetate. The organic layers were combined and then concentrated to an oil. MeOH (80 ml) was added and the resulting slurry was taken on to the next step. $^1$H NMR (CDCl$_3$, 500 MHz): 7.60 (d, 1H), 7.42 (s, 1H), 7.23 (s, 1H), 7.12 (s, 1H), 6.56 (d, 1H), 5.14 (s, 2H), 3.30 (s, 3H), 3.22 (s, 3H), 1.82 (s, 6H).

Step 4

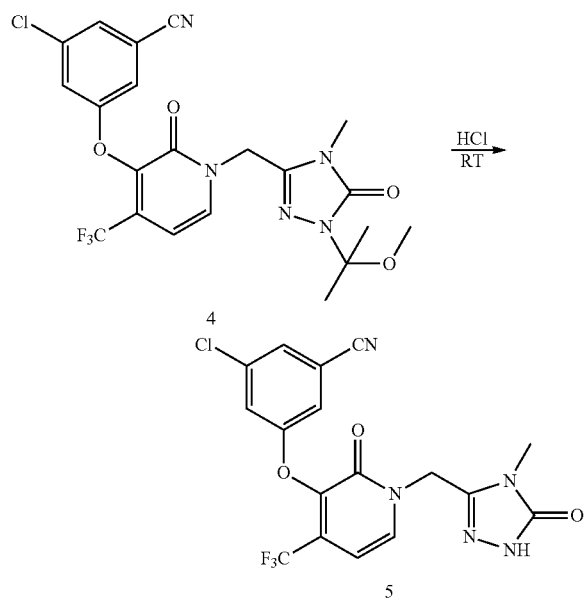

3-Chloro-5-((1-((4-methyl-5-oxo-4,5-dihydro-1H-1,2,4-triazol-3-yl)methyl)-2-oxo-4-(trifluoromethyl)-1,2-dihydropyridin-3-yl)oxy)benzonitrile (5)

To a solution of 4 (5.74 g, 11.53 mmol) in MeOH (from previous step) was added concentrated hydrochloric acid (1 ml, 12.18 mmol) at ambient temperature. The resulting mixture was agitated for 1 hour at room temperature.

The resulting solids were collected by filtration and dried under a nitrogen sweep, providing 5 as a white solid (2.63 g, 46% yield): $^1$H NMR (DMSO, 400 MHz): 11.74 (S, 1H), 7.92 (d, 1H), 7.76 (s, 1H), 7.61 (s, 1H), 7.54 (s, 1H), 6.69 (d, 1H), 5.15 (s, 2H), 3.10 (s, 3H)

Example 2

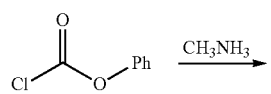

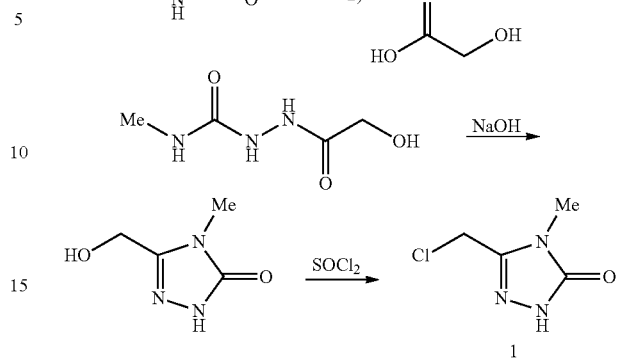

Step 1

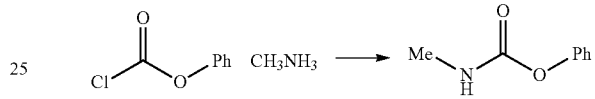

Phenyl Methylcarbamate:

40% Aqueous methylamine (500 g, 6.44 mol) was charged to a 2 L vessel equipped with heat/cool jacket, overhead stirrer, temperature probe and nitrogen inlet. The solution was cooled to −5° C. Phenyl chloroformate (500.0 g, 3.16 mol) was added over 2.5 h maintaining the reaction temperature between −5 and 0° C. On complete addition the white slurry was stirred for 1 h at ~0° C.

The slurry was filtered, washed with water (500 mL) and dried under N$_2$ sweep overnight to afford 465 g (96% yield) of the desired product as a white crystalline solid; 1H NMR (CDCl$_3$, 500 MHz): δ 7.35 (t, J=8.0 Hz, 2H), 7.19 (t, J=8.0 Hz, 1H), 7.12 (d, J=8.0 Hz, 2H), 4.95 (br s, 1H), 2.90 (d, J=5 Hz, 3H).

Step 2

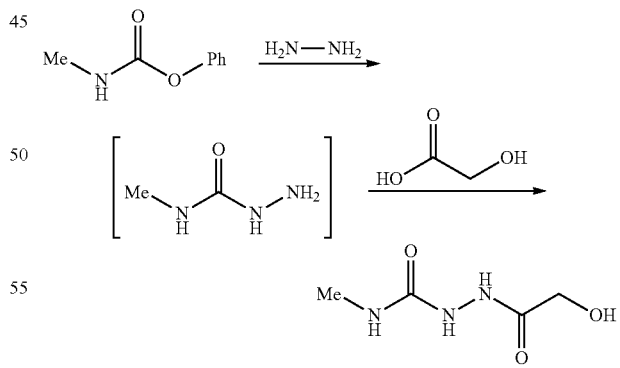

2-(2-Hydroxyacetyl)-N-methylhydrazinecarboxamide

Part A: Phenyl methylcarbamate (300 g, 1.95 mol) was charged to a 2 L vessel with cooling jacket, overhead stirrer, temperature probe, reflux condenser and nitrogen inlet. IPA (390 mL) was added at 23° C. Hydrazine hydrate (119 g, 2.33 mol) was added and the slurry heated to 75° C. for 6 h.

Part B: On complete reaction (>99% conversion by HPLC), IPA (810 mL) and glycolic acid (222 g, 2.92 mol) were added and the mixture stirred at 83-85° C. for 10-12 h. The reaction mixture is initially a clear colorless solution. The mixture is seeded with product (0.5 g) after 4 h at 83-85° C. The slurry was slowly cooled to 20° C. over 2 h and aged for 1 h.

The slurry was filtered and washed with IPA (600 mL). The cake was dried under $N_2$ sweep to afford 241.8 g (81% yield) of the desired product as a white crystalline solid: $^1$H NMR ($D_2O$, 500 MHz): δ 4.11 (s, 2H), 2.60 (s, 3H).

Step 3

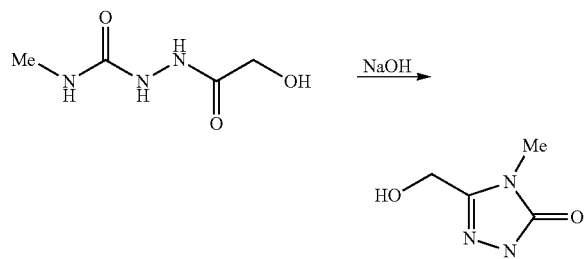

3-(Hydroxymethyl)-4-methyl-1H-1,2,4-triazol-5(4H)-one 2-(2-Hydroxyacetyl)-N-methylhydrazinecarboxamide (130 g @~95 wt %, 0.84 mol), n-propanol (130 mL) and water (130 mL) were charged to a 1 L vessel with jacket, overhead stirrer, temperature probe, reflux condenser and nitrogen inlet. Sodium hydroxide (pellets, 16.8 g, 0.42 mol) was added and the slurry warmed to reflux for 3 h. The reaction mixture was cooled to 20° C. and the pH adjusted to 6.5 (+/−0.5) using conc hydrochloric acid (28.3 mL, 0.34 mol). Water was azeotropically removed under vacuum at 40-50° C. by reducing the volume to ~400 mL and maintaining that volume by the slow addition of n-propanol (780 mL). The final water content should be <3000 ug/mL. The resultant slurry (~400 mL) was cooled to 23° C. and heptane (390 ml) was added. The slurry was aged 1 h at 23° C., cooled to 0° C. and aged 2 h. The slurry was filtered, the cake washed with 1:2 n-PrOH/heptane (100 mL) and dried to provide 125 g (85% yield) of an off-white crystalline solid. The solid is ~73 wt % due to residual inorganics (NaCl): $^1$H NMR ($CD_3OD$, 500 MHz): δ 3.30 (s, 3H), 4.46 (s, 2H).

Step 4

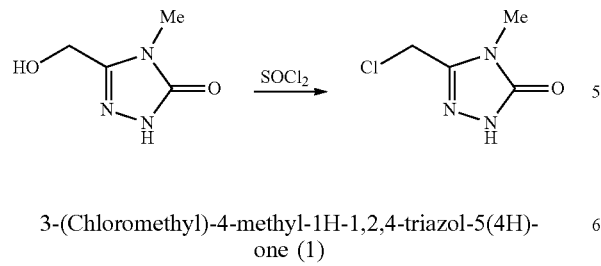

3-(Chloromethyl)-4-methyl-1H-1,2,4-triazol-5(4H)-one (1)

A mixture of 3-(Hydroxymethyl)-4-methyl-1H-1,2,4-triazol-5(4H)-one (54 g, at 73 wt %, 307 mmol) in ethyl acetate (540 mL) was stirred at 45° C. $SOCl_2$ (26.9 mL, 369 mmol) was added over 30-45 min and aged at 50° C. for 2 h. Monitor reaction progress by HPLC. On complete reaction (>99.5% by area at 210 nm), the warm suspension was filtered and the filter cake (mainly NaCl) was washed with ethyl acetate (108 mL). The combined filtrate and wash were concentrated at 50-60° C. under reduced pressure to approximately 150 mL. The resulting slurry was cooled to −10° C. and aged 1 h. The slurry was filtered and the filter cake washed with ethyl acetate (50 mL). The cake was dried under $N_2$ sweep to afford 40.1 g (86% yield) of the desired product as a bright yellow solid: $^1$H NMR ($CD_3OD$, 500 MHz): δ 3.30 (s, 3H), 4.58 (s, 2H).

Example 3

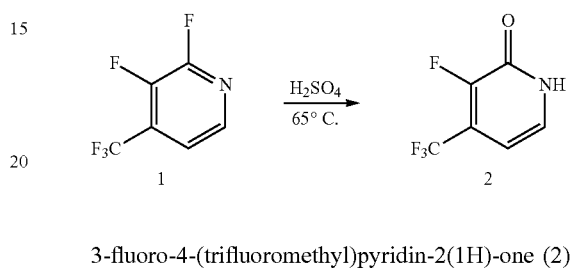

3-fluoro-4-(trifluoromethyl)pyridin-2(1H)-one (2)

To a 250 ml round bottom flask equipped with overhead stirring and a nitrogen inlet was added a mixture of sulfuric acid (24.31 ml, 437 mmol) and water (20.00 ml). To this was added 2,3-difluoro-4-(trifluoromethyl)pyridine (6.83 ml, 54.6 mmol) and the mixture was heated to 65° C. and stirred for 4 h. By this time the reaction was complete, and the mixture was cooled to room temperature. To the flask was slowly added 5M sodium hydroxide (43.7 ml, 218 mmol), maintaining room temperature with an ice bath. The title compound precipitates as a white solid during addition. Stirring was maintained for an additional 1 h after addition. At this time, the mixture was filtered, the filter cake washed with 20 mL water, and the resulting white solids dried under nitrogen. 3-fluoro-4-(trifluoromethyl)pyridin-2(1H)-one (2) was obtained as a white crystalline solid (9.4 g, 51.9 mmol, 95% yield): $^1$H NMR ($CDCl_3$, 400 MHz): 12.97 (br s, 1H), 7.36 (d, 1H), 6.44 (m, 1H).

Example 4

Step 1—Ethyl Ester Synthesis

Experimental Procedure

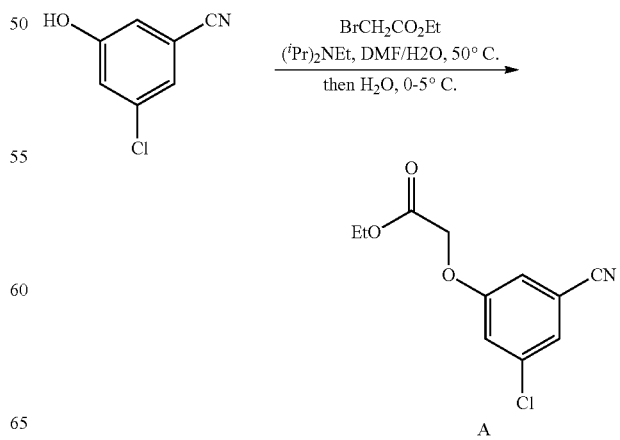

Ethyl 2-(3-chloro-5-cyanophenoxy)acetate (A)

A 1 L round bottom flask equipped with overhead stirring was charged with 3-chloro-5-hydroxybenzonitrile (50.0 g, 98 wt % purity, 319 mmol) and 15% aqueous DMF (200 mL DMF+35.5 mL H$_2$O). To the resulting solution was added diisopropylethylamine (61.3 mL, 99.0% purity, 1.1 equiv) and ethyl 2-bromoacetate (35.7 g, 98% purity, 1.15 equiv) at ambient temperature. The resulting solution was warmed to 50° C. under nitrogen and aged for 12 h. Upon completion of the reaction the batch was cooled to 0-5° C. To the clear to slightly cloudy solution was added 5% seed (3.8 g, 16.0 mmol). H$_2$O (64.5 mL) was added to the thin suspension via syringe pump over 3 h while maintaining the temp at 0-5° C. Additional H$_2$O (200 mL) was added over 1 h while maintaining the temp at 0-5° C. The final DMF/H$_2$O ratio is 1:1.5 (10 vol). The resulting slurry was typically aged 1 h at 0-5° C. The batch was filtered and the cake slurry washed with 2:1 DMF/water (150 mL, 3 vol), followed by water (200 mL, 4 vol). The wet cake was dried on the frit with suction under a nitrogen stream at 20-25° C.; note: heat must not be applied during drying as product mp is 42° C. The cake is considered dry when H$_2$O is <0.2%. Obtained 73.4 g ethyl ester as a light tan solid, 96% yield (corrected), 99.5 LCAP: $^1$H NMR (CDCl$_3$, 400 MHz) δ=7.29 (s, 1H), 7.15 (s, 1H), 7.06 (s, 1H), 4.67 (s, 2H), 4.32 (q, 2H), 1.35 (t, 3H) ppm.

Step 2—Pyridone Synthesis

Synthetic Scheme:

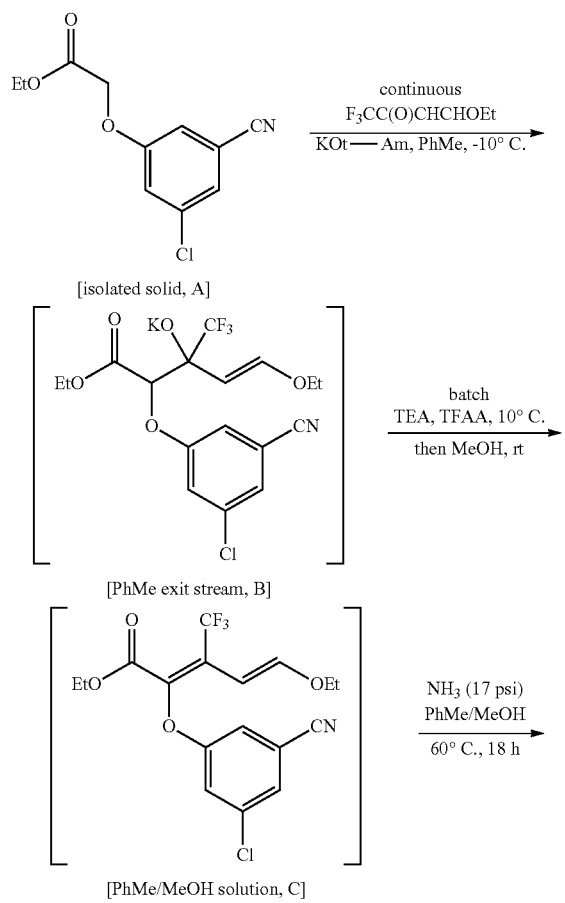

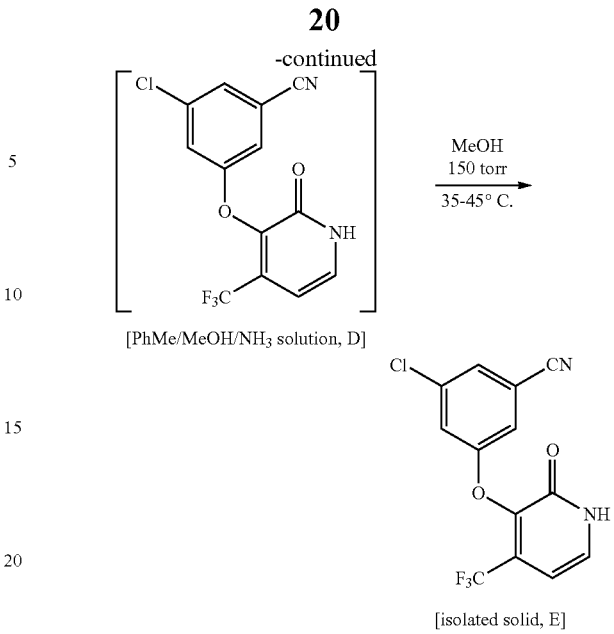

Experimental Procedures

Aldol Condensation, Ester A to Diene C (2E/Z,4E)-Ethyl 2-(3-chloro-5-cyanophenoxy)-5-ethoxy-3-(trifluoromethyl)penta-2,4-dienoate (C)

Ester A (25.01 g, 104.4 mmol, 1.00 equiv) was charged to toluene (113.43 g, 131 mL, 5.24 vol) and 4-ethoxy-1,1,1-trifluoro-3-buten-2-one (26.43 g, 157.2 mmol, 1.51 equiv) was added.

The flow reactor consisted of two feed solution inlets and an outlet to a receiving vessel. The flow reactor schematic is shown in Figure 1.

The ester solution was pumped to one flow reactor inlet. Potassium tert-pentoxide solution was pumped to the second reactor inlet. Trifluoroacetic anhydride was added continuously to the receiver vessel. Triethylamine was added continuously to the receiver vessel.

The flow rates were: 13 mL/min ester solution, 7.8 mL/min potassium tert-pentoxide solution, 3.3 mL/min trifluoroacetic anhydride and 4.35 mL/min triethylamine.

Charged toluene (50 mL, 2 vol) and potassium trifluoroacetate (0.64 g, 4.21 mmol, 0.04 equiv) to the receiver vessel. The flow reactor was submerged in a −10° C. bath and the pumps were turned on. The batch temperature in the receiver vessel was maintained at 5 to 10° C. throughout the run using a dry ice/acetone bath. After 13.5 min the ester solution was consumed, the reactor was flushed with toluene (10 mL) and the pumps were turned off.

The resulting yellow slurry was warmed to room temperature and aged for 4.5 h. Charged methanol (160 mL) to afford a homogeneous solution which contained 81.20 area percent diene C by HPLC analysis.

The solution of diene C (573 mL) was used without purification in the subsequent reaction.

Cyclization, Diene C to E

3-Chloro-5-((2-oxo-4-(trifluoromethyl)-1,2-dihydropyridin-3-yl)oxy)benzonitrile (E)

To a solution of diene C in PhMe/MeOH (573 mL; 40.69 g, 104.4 mmol theoretical C) was charged methanol (25 mL, 0.61 vol). Ammonia (32 g, 1.88 mol, 18 equiv based on theoretical C) was added and the solution was warmed to 60° C. The reaction was aged at 60° C. for 18 h. The temperature was adjusted to 35-45° C. and the pressure was decreased maintain a productive distillation rate. The batch volume was reduced to ~300 mL and methanol (325 mL, 8 vol) was charged in portions to maintain a batch volume between 250 and 350 mL. The heating was stopped and the system vented. The resulting slurry was cooled to room temperature and aged overnight.

The batch was filtered and the cake washed with methanol (3×, 45 mL). The wet cake was dried on the frit with suction under a nitrogen stream to afford 18.54 g of a white solid: $^1$H NMR (DMSO-$d_6$, 500 MHz): δ 12.7 (br s, 1H), 7.73 (t, 1H, J=1.5 Hz), 7.61-7.59 (m, 2H), 7.53 (t, 1H, J=2.0 Hz), 6.48 (d, 1H, J=7.0 Hz) ppm.

Step 3—Chlorination, Alkylation and Isolation of 3-Chloro-5-({1-[(4-methyl-5-oxo-4,5-dihydro-1H-1,2,4-triazol-3-yl)methyl]-2-oxo-4-(trifluoromethyl)-1,2-dihydropyridin-3-yl}oxy)benzonitrile

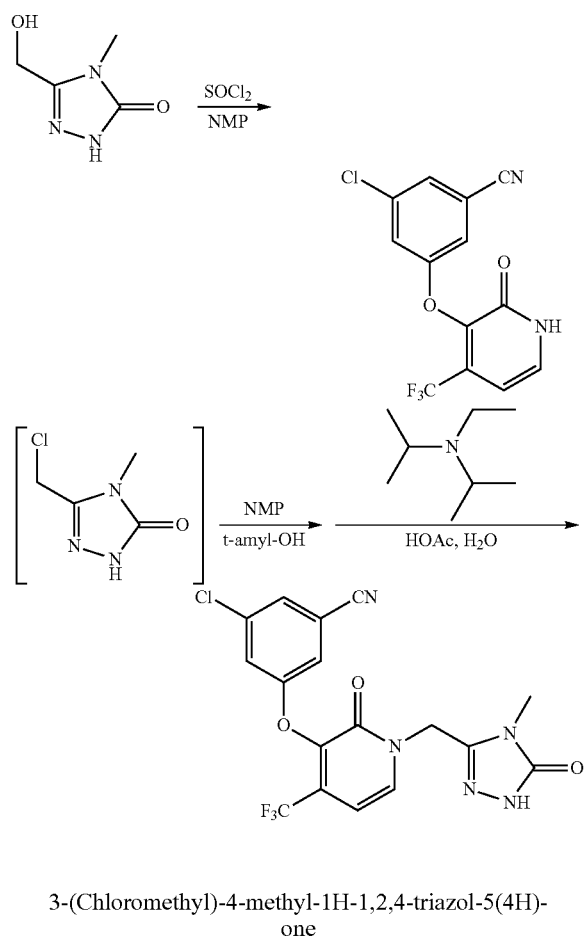

3-(Chloromethyl)-4-methyl-1H-1,2,4-triazol-5(4H)-one 3-(Hydroxymethyl)-4-methyl-1H-1,2,4-triazol-5(4H)-one (1.638 kg of 68 wt %, 8.625 mol) and N-methylpyrrolidinone (8.9 L) was charged into a 30 L vessel. The suspension was aged for 10 h at ambient temperature. The slurry was filtered through a 4 L sintered glass funnel under N$_2$ and the filter cake (mainly NaCl) was washed with NMP (2.23 L). The combined filtrate and wash had a water content of 5750 µg/mL. The solution was charged to a 75 L flask equipped with a 2N NaOH scrubber to capture off-gasing vapors. Thionyl chloride (0.795 L, 10.89 mol) was added over 1 h and the temperature rose to 35° C. HPLC analysis indicated that the reaction required an additional thionyl chloride charge (0.064 L, 0.878 mol) to bring to full conversion. The solution was warmed to 50° C., placed under vacuum at 60 Torr (vented to a 2N NaOH scrubber), and gently sparged with subsurface N$_2$ (4 L/min) The degassing continued for 10 h until the sulfur dioxide content in the solution was <5 mg/mL as determined by quantitative GC/MS. The tan solution of 3-(chloromethyl)-4-methyl-1H-1,2,4-triazol-5(4H)-one in NMP weighed 13.0 kg and was assayed at 9.63 wt % providing 1.256 kg (97% yield).

3-chloro-5-((1-((4-methyl-5-oxo-4,5-dihydro-1H-1,2,4-triazol-3-yl)methyl)-2-oxo-4-(trifluoromethyl)-1,2-dihydropyridin-3-yl)oxy)benzonitrile To a 75 L flask was charged a 9.63 wt % solution of 3-(chloromethyl)-4-methyl-1H-1,2,4-triazol-5(4H)-one in NMP (11.6 kg, 7.55 mol), 3-chloro-5-((2-oxo-4-(trifluoromethyl)-1,2-dihydropyridin-3-yl)oxy)benzonitrile (2.00 kg, 6.29 mol), NMP (3.8 L) and 2-methyl-2-butanol (6.0 L). To the resulting suspension was slowly added N,N-diisopropylethylamine (4.38 L, 25.2 mol) over 4 h. The reaction was aged 18 h at ambient temperature. The reaction is considered complete when HPLC indicates <1% 3-chloro-5-((2-oxo-4-(trifluoromethyl)-1,2-dihydropyridin-3-yl)oxy)benzonitrile remaining. The tan solution was quenched with acetic acid (1.26 L, 22.0 mol) and aged at ambient temperature overnight. The tan solution was warmed to 70° C. Water (2.52 L) was added and the batch was seed with anhydrate Form II (134 g). The thin suspension was aged 1 h at 70° C. Additional water (14.3 L) was added evenly over 7 h. The slurry was aged 2 h at 70° C. and then slowly cooled to 20° C. over 5 h. The slurry was filtered and washed with 2:1 NMP/water (6 L), followed by water washes (6 L×2). The filter cake was dried over a N$_2$ sweep to give 2.53 kg (85% yield—corrected) of a white solid that was confirmed to be crystalline Form II by X-ray powder defraction analysis.

What is claimed is:

1. A method for synthesizing a compound of Formula I

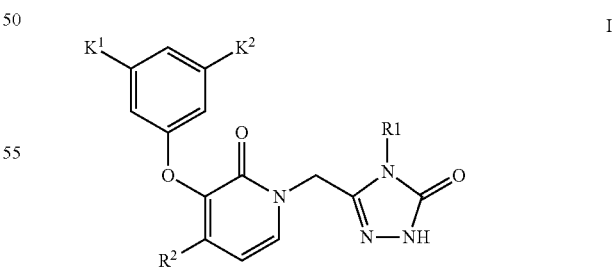

wherein R$^1$ is C$_{1-6}$ alkyl, K$^1$ and K$^2$ are independently CH$_3$, CF$_3$, CHF$_2$, CH$_2$CF$_3$, OCH$_3$, Cl, Br, F, CN or SCH$_3$, and R$^2$ is CF$_3$, Cl or Br, comprising synthesizing the compound of Formula A by condensing glycolic acid with a compound of Formula G

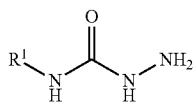

to yield a compound of Formula H

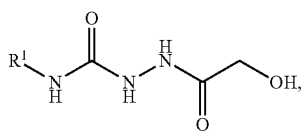

cyclizing the compound of Formula H under first basic conditions to make a compound of Formula J

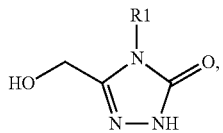

replacing the alcohol with the leaving group $X^1$ by reacting the compound of Formula J with an activating agent to yield a compound of Formula A

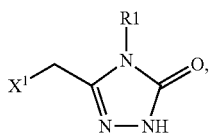

and coupling the compound of Formula A, wherein the compound of Formula A is not isolated after its synthesis, with a compound of Formula N

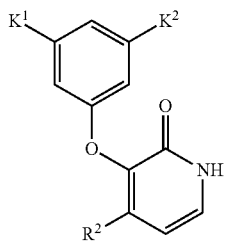

in the presence of a first base selected from an inorganic base or a tertiary amine base in a polar aprotic solvent to yield the compound of Formula I.

2. The method for synthesizing a compound of Formula I according to claim 1 wherein $X^1$ is chloro and the activating agent is $SOCl_2$.

3. The method for synthesizing a compound of Formula I according to claim 1 wherein first basic conditions means in the presence of sodium hydroxide.

4. The method for synthesizing a compound of Formula I according to claim 1 further comprising synthesizing the compound of Formula G by reacting a compound of Formula K

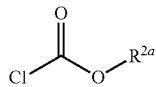

wherein $R^{2a}$ is selected from aryl or heteroaryl, wherein said aryl or heteroaryl are optionally substituted with one or more substituents up to the maximum number allowed by valence selected from the group consisting of: halogen, $C_{1-6}$ alkyl, $C_{1-6}$ haloalkyl, OH, O—$C_{1-6}$ alkyl, O—$C_{1-6}$ haloalkyl, $N(R^A)R^B$, $C(O)N(R^A)R^B$, $C(O)R^A$, $CO_2R^A$, $SO_2R^A$, $N(R^A)C(O)N(R^A)R^B$, or $N(R^A)CO_2R^B$; and $R^A$ and $R^B$ are independently selected from H, $C_{1-6}$ alkyl and $C_{3-6}$ cycloalkyl, wherein said $C_{1-6}$ alkyl and $C_{3-6}$ cycloalkyl are optionally substituted with one or more substituents up to the maximum number allowed by valence selected from the group consisting of: halogen, OH, CN, $C_{1-4}$ alkoxy, $C_{3-6}$ cycloalkyl and phenyl;

with a compound of Formula L

under second basic conditions to yield a compound of Formula M

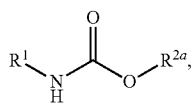

and reacting the compound of Formula M with hydrazine to yield a compound of Formula G.

5. A method for synthesizing a compound of Formula I

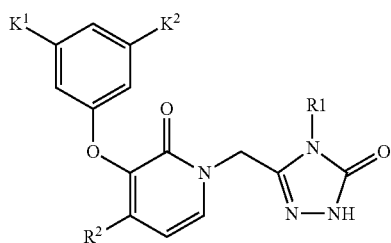

wherein $R^1$ is $C_{1-6}$ alkyl, $K^1$ and $K^2$ are independently $CH_3$, $CF_3$, $CHF_2$, $CH_2CF_3$, $OCH_3$, Cl, Br, F, CN or $SCH_3$, and $R^2$ is $CF_3$, Cl or Br, comprising introducing a nitrogen protecting group PG into a compound of Formula A

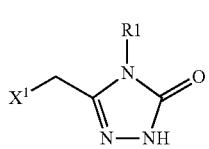

wherein X¹ is a leaving group, to make a compound of Formula B

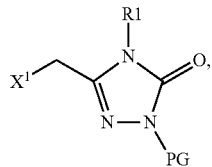

reacting the compound of Formula B with a compound of Formula C

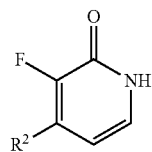

in the presence of a first base selected from an inorganic base or a tertiary amine base in a first polar aprotic solvent to make a compound of Formula D

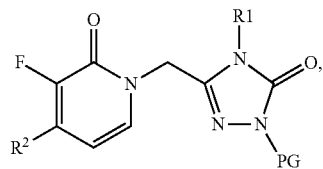

coupling the compound of Formula D with a compound of Formula E

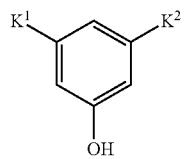

to make a compound of Formula F

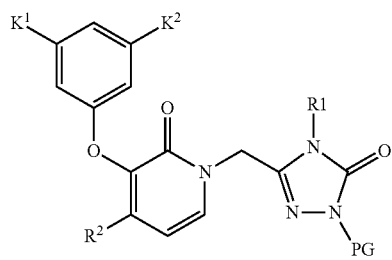

by way of step (1) or step (2) wherein:
step (1) comprises adding the compound of Formula E to the reaction mixture comprising the compound of Formula D from the previous step without further isolation to make a compound of Formula F, and step (2) comprises isolating the compound of Formula D from the previous step and reacting the compound of Formula D with the compound of Formula E in the presence of a second base selected from an inorganic base or a tertiary amine base in a second polar aprotic solvent to yield the compound of Formula F, and deprotecting the nitrogen by removing the protecting group PG in the compound of Formula F to yield the compound of Formula I.

6. The method for synthesizing the compound of Formula I according to claim 5 wherein PG is selected from the group consisting of: $C_{1-6}$ alkyl, vinyl, C(O)—O-L, C(O)-L, aryl, hetroaryl, benzyl, benzhydryl, trityl, anthranyl and $C_{1-6}$alkoxymethyl, wherein aryl, heteroaryl, benzyl, benzyhydryl and trityl optionally are substituted with 1 to 3 substituents independently selected from methoxy and nitro, $C_{1-6}$alkoxymethyl is optionally substituted with trimethylsilyl and L is $C_{1-6}$alkyl, aryl or benzyl.

7. The method for synthesizing the compound of Formula I according to claim 6 wherein PG is 2-methoxypropan-2-yl.

8. The method for synthesizing the compound of Formula I according to claim 5 wherein X¹ is selected from the group consisting of: halogen, OMs, OTs, OBs, $OP(O)(OR^i)_4$, $OC(O)R^i$, $OC(O)OR^i$ and $OC(O)NR^iR^{ii}$, wherein $R^i$ and $R^{ii}$ are independently selected from H and $C_{1-6}$alkyl.

9. The method for synthesizing the compound of Formula I according to claim 8 wherein X¹ is chloro.

10. The method for synthesizing the compound of Formula I according to claim 5 wherein the first base is potassium carbonate and the first polar aprotic solvent is dimethylformamide.

11. The method for synthesizing the compound of Formula I according to claim 10 wherein the compound of Formula F is made by step (1).

12. The method for synthesizing the compound of Formula I according to claim 5 wherein the nitrogen protecting group PG in the compound of Formula F is deprotected by reacting the compound of Formula F with an acid.

13. A method for synthesizing a compound of Formula A

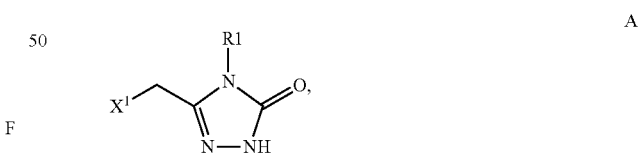

comprising condensing glycolic acid with a compound of Formula G

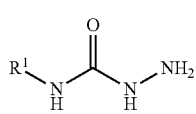

to yield a compound of Formula H

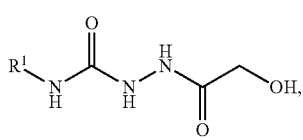

cyclizing the compound of Formula H under basic conditions to make a compound of Formula J

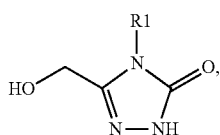

and replacing the alcohol with the leaving group $X^1$ by reacting the compound of Formula J with an activating agent to yield the compound of Formula A.

14. The method for synthesizing a compound of Formula A according to claim 13 wherein $X^1$ is chloro and the activating agent is $SOCl_2$.

15. The method for synthesizing a compound of Formula A according to claim 13 wherein basic conditions means in the presence of sodium hydroxide.

16. The method for synthesizing the compound of Formula I according to claim 1 wherein $K^1$ is Cl, $K^2$ is CN, $R^1$ is $CH_3$ and $R^2$ is $CF_3$.

17. The method for synthesizing the compound of Formula I according to claim 5 wherein $K^1$ is Cl, $K^2$ is CN, $R^1$ is $CH_3$ and $R^2$ is $CF_3$.

18. A method for synthesizing a compound of Formula I

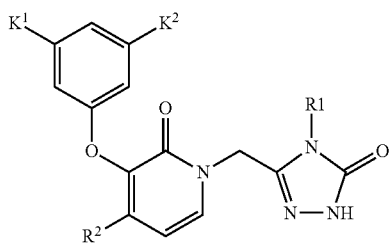

wherein $R^1$ is $C_{1-6}$ alkyl, $K^1$ and $K^2$ are independently $CH_3$, $CF_3$, $CHF_2$, $CH_2CF_3$, $OCH_3$, Cl, Br, F, CN or $SCH_3$, and $R^2$ is $CF_3$, Cl or Br, comprising:
1) reacting the compound of Formula J

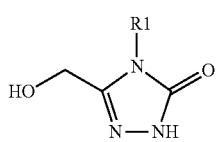

with $SOCl_2$ to yield a compound of Formula A-i

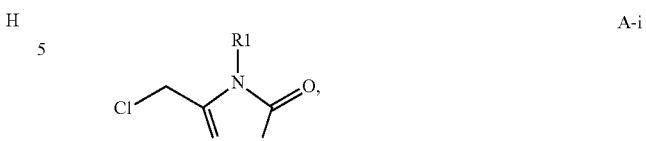

2) sparging the solution of the compound of Formula A-i with nitrogen to reduce the content of sulfur dioxide in the solution, and
3) coupling the compound of Formula A-i with a compound of Formula N

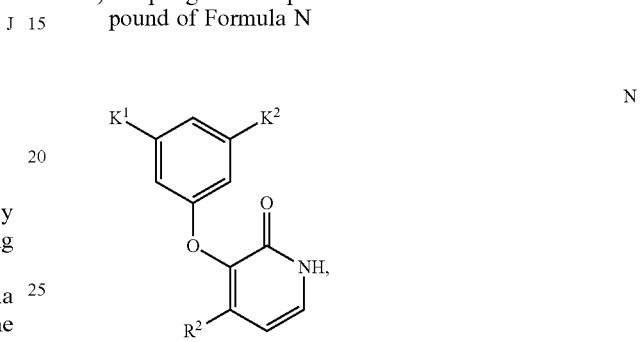

wherein the compound of Formula A-i is not isolated after its synthesis and is in situ reacted with
the compound of Formula N in the presence of a base selected from an inorganic base or a tertiary amine base in a polar aprotic solvent to yield the compound of Formula I.

19. The method for synthesizing the compound of Formula I according to claim 18 wherein the base is N,N-diisopropylethylamine.

20. The method for synthesizing the compound of Formula I according to claim 18 wherein the polar aprotic solvent is N-methylpyrrolidinone.

21. The method for synthesizing the compound of Formula I according to claim 18 wherein $K^1$ is Cl, $K^2$ is CN, $R^1$ is $CH_3$ and $R^2$ is $CF_3$.

22. The method for synthesizing the compound of Formula I according to claim 21 wherein in step 2, the solution of the compound of Formula A-i is warmed during sparging with $N_2$.

23. The method for synthesizing the compound of Formula I according to claim 22 wherein in step 2, the solution of the compound of Formula A-i is sparged with $N_2$ under vacuum.

24. The method for synthesizing the compound of Formula I according to claim 18 wherein in step 1, the compound of Formula J is reacted with $SOCl_2$ in N-methylpyrrolidinone.

25. The method for synthesizing the compound of Formula I according to claim 18 wherein:
$K^1$ is Cl, $K^2$ is CN, $R^1$ is $CH_3$ and $R^2$ is $CF_3$,
the compound of Formula J is reacted with $SOCl_2$ in N-methylpyrrolidinone,
the base is N,N-diisopropylethylamine,
the polar aprotic solvent is N-methylpyrrolidinone, and
in step 2 the solution of the compound of Formula A-i is warmed and is sparged with $N_2$ under vacuum.

* * * * *